United States Patent
Quinn et al.

(10) Patent No.: US 8,226,823 B2
(45) Date of Patent: Jul. 24, 2012

(54) SALOMETER AND FLOW RATE SENSOR ASSEMBLY

(75) Inventors: Kerry Quinn, Palatine, IL (US); Gene Wayman, Fox River Grove, IL (US); Kumudika Premathilake, Schaumburg, IL (US); Bill Lathouris, Palatine, IL (US)

(73) Assignee: Culligan International Company, Rosemont, IL (US)

( * ) Notice: Subject to any disclaimer, the term of this patent is extended or adjusted under 35 U.S.C. 154(b) by 969 days.

(21) Appl. No.: 12/198,258

(22) Filed: Aug. 26, 2008

(65) Prior Publication Data

US 2009/0056422 A1 Mar. 5, 2009

Related U.S. Application Data

(60) Provisional application No. 60/966,368, filed on Aug. 27, 2007.

(51) Int. Cl.
*B01D 35/14* (2006.01)

(52) U.S. Cl. ............ 210/87; 73/219; 210/140; 210/190; 340/606

(58) Field of Classification Search .................... 210/86, 210/87, 94, 121, 138–141, 190, 191, 269, 210/739; 73/861, 861.05, 239, 221–224, 73/219; 340/606
See application file for complete search history.

(56) References Cited

U.S. PATENT DOCUMENTS

| | | | |
|---|---|---|---|
| 1,980,161 A | 11/1934 | Applebaum | |
| 2,209,487 A | 7/1940 | Wagner | |
| 2,415,936 A | 2/1947 | Contant et al. | |
| 2,614,578 A * | 10/1952 | Stickney | 137/391 |
| 2,659,068 A | 11/1953 | Erickson et al. | |
| 2,919,805 A | 1/1960 | Nickols | |
| 3,531,402 A * | 9/1970 | Thompson | 252/175 |
| 3,662,598 A * | 5/1972 | Spencer | 73/861.05 |
| 3,722,276 A | 3/1973 | Chandler et al. | |
| 3,755,804 A | 8/1973 | Johnson | |
| 3,777,574 A | 12/1973 | Brown et al. | |
| 3,899,421 A | 8/1975 | Keilin et al. | |
| 4,154,677 A | 5/1979 | Mantell | |
| 4,237,538 A * | 12/1980 | Le Dall | 700/282 |
| 4,240,291 A * | 12/1980 | Andersson et al. | 73/861.05 |
| 4,320,010 A | 3/1982 | Tucci et al. | |
| 4,385,357 A | 5/1983 | Davis et al. | |
| 4,568,465 A | 2/1986 | Davis et al. | |
| 4,668,402 A * | 5/1987 | Norton | 210/662 |
| 4,802,362 A * | 2/1989 | Haynes | 73/249 |
| 4,847,598 A | 7/1989 | Tucci et al. | |
| 4,880,513 A | 11/1989 | Davis et al. | |
| 4,897,797 A | 1/1990 | Free, Jr. et al. | |
| 5,022,994 A | 6/1991 | Avery et al. | |

(Continued)

FOREIGN PATENT DOCUMENTS

EP  0114 039 B1  3/1987

(Continued)

*Primary Examiner* — Joseph Drodge
(74) *Attorney, Agent, or Firm* — Greer, Burns & Crain, Ltd.

(57) ABSTRACT

A salometer and flow rate sensor assembly for a water softener system including a brine tank containing a brine solution including at least one sensor housing provided in the brine tank, a first detector set associated with the housing and configured for indicating whether the brine solution is adequately concentrated and a second detector set associated with the housing and configured for measuring the brine solution flow rate during brine draw and refill cycles of regeneration.

11 Claims, 2 Drawing Sheets

U.S. PATENT DOCUMENTS

| | | |
|---|---|---|
| 5,104,553 A | 4/1992 | Lorenz et al. |
| 5,231,883 A | 8/1993 | Lefebvre et al. |
| 5,234,601 A | 8/1993 | Janke et al. |
| 5,239,285 A | 8/1993 | Rak |
| 5,792,343 A * | 8/1998 | Fujita et al. .................. 210/96.1 |
| 6,228,255 B1 * | 5/2001 | Peterson et al. ................ 210/90 |
| 6,238,567 B1 | 5/2001 | Van de Moortele |
| 6,393,898 B1 * | 5/2002 | Hajduk et al. ............... 73/54.05 |
| 6,408,694 B1 | 6/2002 | Lin et al. |
| 6,646,443 B2 | 11/2003 | Higo |
| 6,696,963 B2 | 2/2004 | Zimmerman et al. |
| 6,696,966 B2 | 2/2004 | Bearak |
| 6,776,913 B1 * | 8/2004 | Jangbarwala ................ 210/677 |
| 6,783,684 B2 | 8/2004 | Teel, Jr. |
| 6,790,362 B2 | 9/2004 | FitzGerald et al. |
| 7,030,768 B2 | 4/2006 | Wanie |
| 2003/0106370 A1 | 6/2003 | Fearnside et al. |
| 2003/0172732 A1 * | 9/2003 | Jacek .............................. 73/219 |
| 2005/0000902 A1 | 1/2005 | Newenhizen et al. |
| 2005/0006311 A1 | 1/2005 | Reif |
| 2006/0086648 A1 | 4/2006 | Sieth et al. |
| 2006/0266710 A1 | 11/2006 | Premathilake et al. |

FOREIGN PATENT DOCUMENTS

FR        2752297 A1    2/1998

\* cited by examiner

SALOMETER AND FLOW RATE SENSOR ASSEMBLY

PRIORITY CLAIM

This application claims priority to and the benefit of U.S. Provisional Application No. 60/966,368 filed on Aug. 27, 2007.

BACKGROUND

The present sensor assembly relates to a sensor for a water treatment system, and more particularly to a salometer and flow rate sensor assembly for a brine tank in a water treatment system.

Water softeners are well known in the art and typically include a treatment tank containing an ion exchange resin and a brine tank containing a brine solution. Water softening occurs by running water through the ion exchange resin which replaces the calcium and magnesium cations in the water with sodium cations. As the ion exchange process continues, the resin eventually loses its capacity to soften water and must be replenished with sodium cations. The process by which the calcium and magnesium ions are removed, the capacity of the ion exchange resin to soften water is restored and the sodium ions are replenished is known in the art as regeneration.

During regeneration, brine, a concentrated or saturated salt solution, is passed through the ion exchange resin and the cations in the ion exchange resin are replaced with sodium ions. Regeneration is a multi-step process incorporating a number of cycles, specifically, backwash, brine draw, slow rinse, fast rinse and refill cycles. During the backwash cycle, flow into the treatment tank is reversed to remove sediment from the ion exchange resin.

During the brine draw cycle, highly concentrated sodium chloride or potassium chloride brine is introduced into the ion exchange resin, where the sodium or potassium ions in the brine solution displace the calcium and magnesium ions attached to the ion exchange beads in the resin. The brine draw flow rate is dependent on two main variables—the condition of the eductor nozzle and throat and influent pressure. The eductor nozzle enables the brine solution to flow out of the brine tank through a conduit (throat) and into the treatment tank through an inflow conduit. Plugged or partially blocked eductor nozzles and/or low pressure through the conduits can lead to reduced brine draw flow rates, which can result in an extended brine rinse cycle, unnecessary waste of regeneration water volume and inefficient regeneration of the ion exchange resin. Accordingly, there is a need for an improved water treatment system that alerts the user when the eductor nozzles are clogged and need servicing.

When an adequate level of ion exchange has taken place, used brine is rinsed off the ion exchange resin in the treatment tank during the slow rinse and fast rinse cycles. During the refill cycle, soft water flows through an outflow conduit in the treatment tank and through the conduit in the brine tank, filling the brine tank with soft water to prepare the brine solution for the next regeneration. Plugged or partially blocked refill flow controls/lines in the conduits can lead to reduced refill flow rates, which can result in reduced brine volume in the salt storage tank and to a lower than desired salt dosage in a subsequent regeneration. A reduced salt dosage will result in insufficient regeneration of the ion exchange resin, and a reduction in service capacity and hardness leakage. Accordingly, there is a need for an improved water treatment system that alerts the user when the refill flow lines are clogged and need servicing.

Water softener systems are generally installed in environments with varying temperature and humidity conditions, some of which are more conducive than others to "salt bridging" in the brine tank. A "salt bridge" is a hard crust of salt that forms from a reaction between the salt and humidity in the brine tank, leading to low concentration brine under the "salt bridge" because the salt forming the bridge is unable to dissolve in the water to make brine. This leads to an ineffective ion exchange reaction during the regeneration cycle, and results in service capacity reduction and hardness leakage. Therefore, there is a need for an improved water treatment system that indicates the presence of a salt bridge and enables the user to remove the bridge.

SUMMARY

The present salometer and flow rate sensor assembly meets or exceeds each of the above indicated needs by being configured for determining brine draw and refill flow rates. Further, the present salometer and flow rate sensor assembly is constructed and arranged for indicating whether the brine solution is sufficiently concentrated and for determining the presence of a "salt bridge" in the brine tank.

More specifically, the present invention provides a salometer and flow rate sensor assembly for a water softener system including a brine tank containing a brine solution. The assembly includes at least one sensor housing provided in the brine tank, a first detector set associated with the housing and configured for indicating whether the brine solution is adequately concentrated and a second detector set associated with the housing and configured for measuring the brine solution flow rate during brine draw and refill cycles of regeneration.

The present invention also provides a method for determining a flow rate of a brine solution in a brine tank is provided where the brine tank includes a sensor housing having a first pair of detectors including a first photo emitter and a first photo detector, a second pair of detectors including a second photo emitter and a second photo detector, a movable float located in a cavity between the first and second photo emitters and the first and second photo detectors and a timer in communication with the first and second pairs of detectors. The method includes the steps of starting the timer when the float is at a first position relative to the first and second pairs of detectors, stopping the timer when the float is at a second position relative to the first and second pairs of detectors, determining a total time taken for the float to move from the first position to the second position and calculating a flow rate based on the total time.

The present invention further provides a method for determining the presence of a salt bridge in a brine solution stored in a brine tank is provided where the brine tank includes a sensor housing having a first pair of detectors including a first photo emitter and a first photo detector, a second pair of detectors including a second photo emitter and a second photo detector, a movable float located in a cavity between the first and second photo emitters and the first and second photo detectors and a timer in communication with the first and second pairs of detectors. The method includes the steps of starting the timer when the float is at a first position relative to the first pair of detectors, stopping the timer when the float is at a second position relative to the second pair of detectors, determining a total time taken for the float to move from the first position to the second position; calculating a first average velocity of the brine solution below the second pair of detectors, calculating a second average velocity of the brine solution above the second pair of detectors, determining a velocity ratio based on the first average velocity and the second average velocity and activating at least one indicator when the velocity ratio is at a designated velocity ratio.

DETAILED DESCRIPTION

Figure 1:
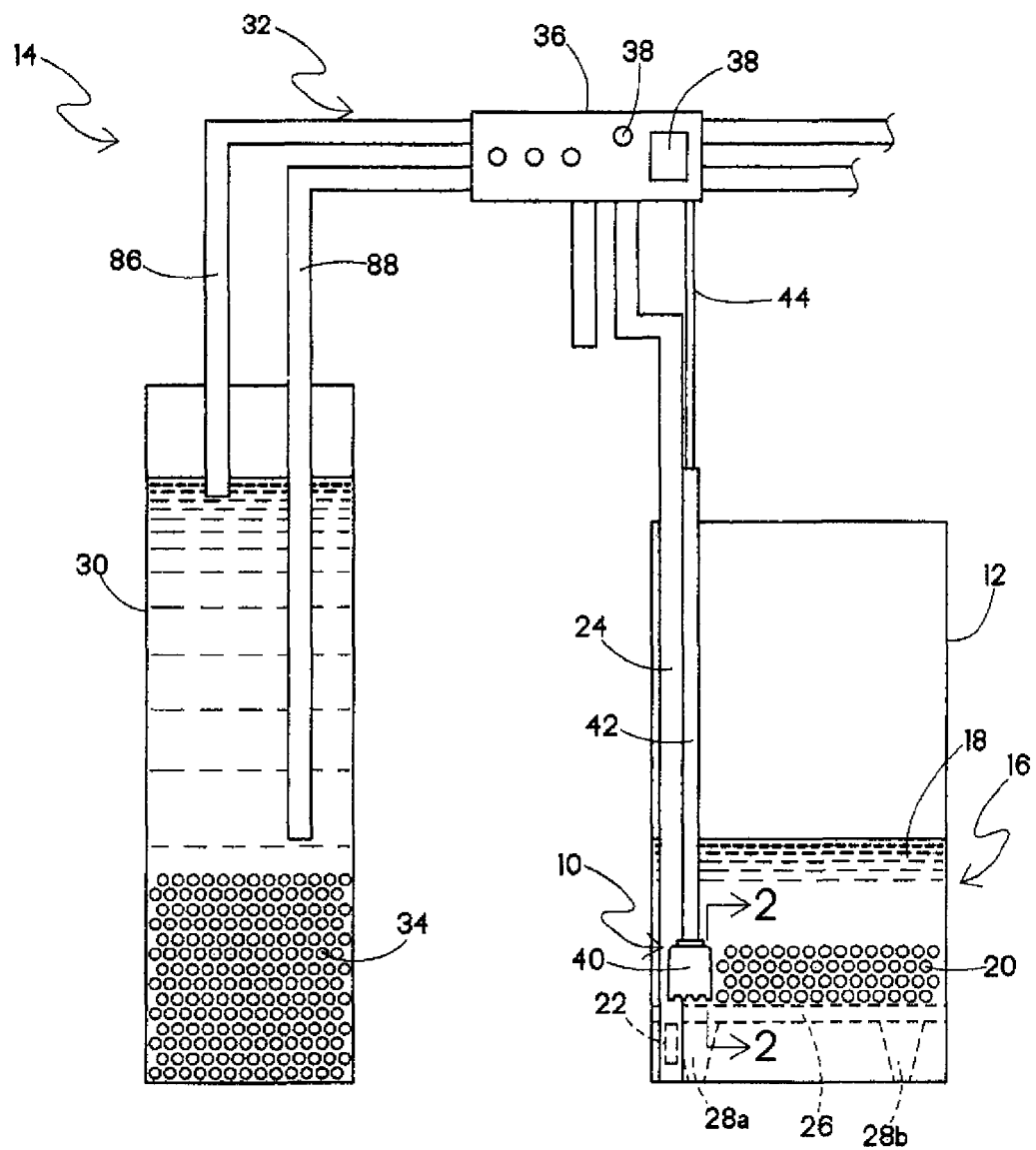
FIG. 1 is a schematic diagram of a water treatment system including the present salometer and flow rate sensor assembly provided in a sensor housing in a brine tank.
Figure 2:
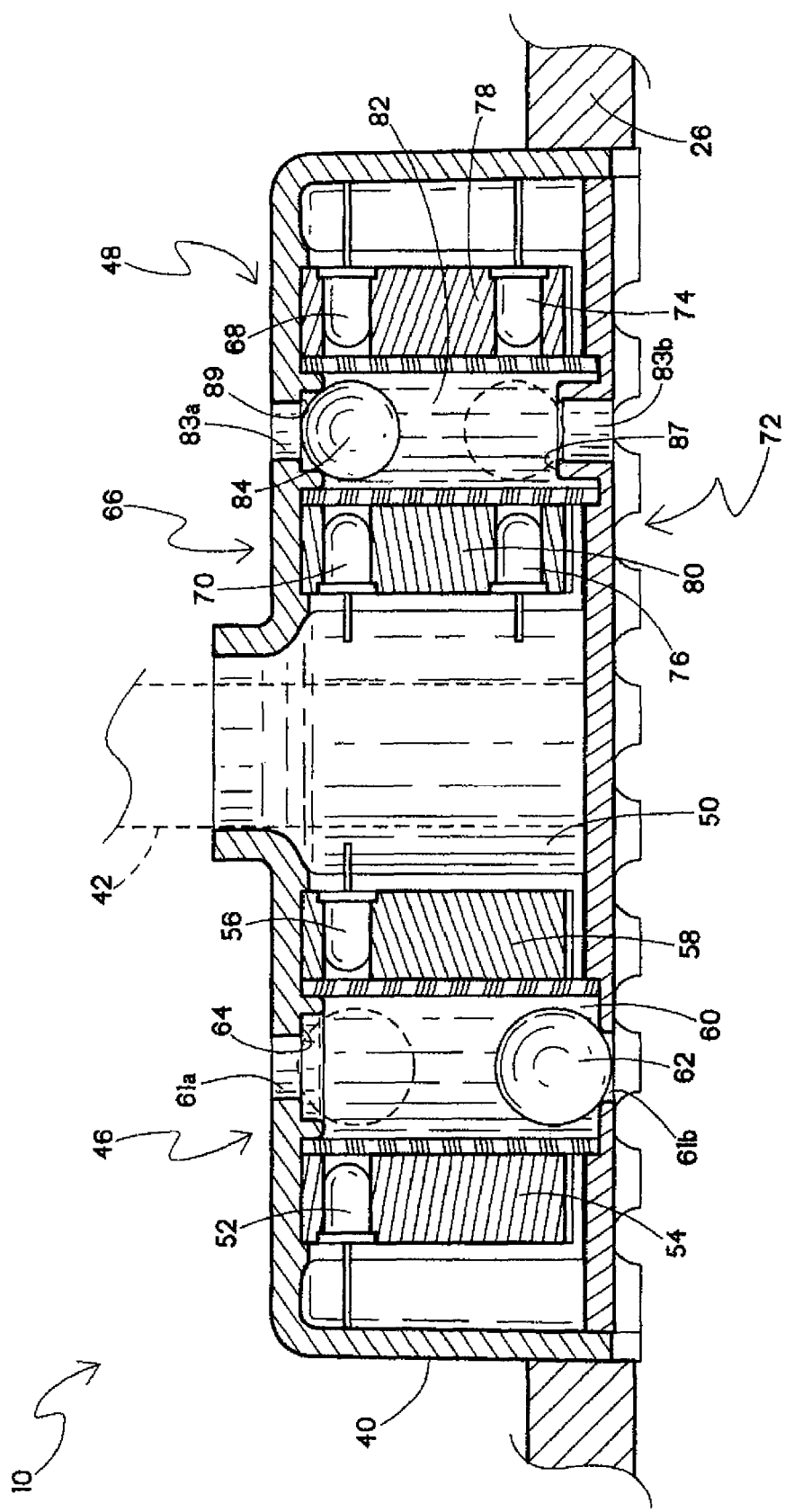
FIG. 2 is a cross-section of the sensor housing taken along the line 2-2 in FIG. 1 and in the direction indicated.

Referring to FIGS. 1 and 2, the present salometer and flow rate sensor assembly is generally designated 10 and is provided within a brine tank 12 of a water softener system 14. As known in the art, the brine tank 12 contains a brine solution 16 including brine 18 and salt granules 20. The brine tank 12 further includes a brine valve 22 (shown hidden) provided in a brine valve housing or conduit 24. A suitable brine valve is disclosed in U.S. Pat. No. 6,551,504, which is incorporated herein by reference. A brine plate 26 (shown hidden) has preferably frusto-conical shaped support legs 28a, 28b (shown hidden), which suspend the plate above a bottom of the tank 12, although other shapes for the legs are contemplated. As known in the art, the salt granules 20 rest upon the brine plate 26, which assists in dissolving salt, protects the system 14 from salt impurities, and is generally manufactured of a corrosion-resistant material, such as plastic, although other materials with similar anti-corrosion properties are contemplated.

A treatment tank 30 is connected to the brine tank 12 through valves and pipe or tubing generally designated 32, and contains a supply of preferably granular resin 34, as known in the art. The water softener system 14 further includes a controller 36 having a microprocessor (not shown) or the like and displays and/or indicators 38 configured for alerting a user of the status of the water softener system 14. As known in the art, the indicators 38 can be audible and/or visible.

The sensor assembly 10 includes a sensor housing 40 and a salt wand 42 attached to the sensor housing and extending out of the brine tank 12. The wand 42 protects wiring 44 extending from the sensor housing 40 to the controller 36. Preferably, both the sensor housing 40 and the salt wand 42 are manufactured from plastic, which is generally resistant to salt corrosion, although other materials with similar anti-corrosion properties are contemplated. As will be discussed in further detail below, the sensor assembly 10 communicates with the microprocessor in the controller 36, which is configured for calculating the flow rates/salinity of the brine solution 16.

As seen in FIG. 2, the sensor housing 40 is in fluid communication with the brine solution 16 in the tank 12 and includes a first detector set 46 and a second detector set 48 disposed on opposite sides of the sensor housing and defining a cavity 50 therebetween for receiving the salt wand 42 (shown hidden).

The first detector set 46 is configured for determining whether the brine solution 16 is adequately concentrated and indicating the need for salt replenishment in the brine tank 12. Included in the first detector set 46 is a photo emitter 52 disposed in a first chamber 54 and a photo detector 56 facing the photo emitter and disposed in a second chamber 58 spaced apart from the first chamber, defining a first float cavity 60 therebetween. The first float cavity 60 includes openings 61a, 61b that are in fluid communication with the brine solution 16 in the brine tank 12. Preferably, the photo emitter 52 is arranged at the same height as the photo detector 56 so that both components are aligned with each other. The photo emitter 52 produces an infrared ("IR") light, and the photo detector 56 passes an electrical current that is directly proportional to the IR light intensity produced by the photo emitter, which will be described in further detail below. It should be appreciated that the position of the photo emitter and the photo detector is reversible.

A float 62, preferably a ball-type float having a specific density of approximately 1.12-1.15 (i.e., approximately 1.12-1.15 times greater than the specific density of water), is located in the first float cavity 60 between the photo emitter 52 and the photo detector 56. The float 62 is preferably manufactured of a corrosion-resistant polymer having the above-recited density, although it is appreciated that other plastics or materials with similar anti-corrosion properties may be suitable. By having the recited density, the float 62 will not move unless the brine solution 16 has a density equal to or greater than the float density, indicating that the brine solution is sufficiently concentrated.

During the entire regeneration cycle, when the density of the brine solution 16 is greater than that of the float 62, the float is suspended at a top 64 of the first float cavity 60 (shown in dashed lines in FIG. 2), adjacent to the opening 61a. At this position, the float 62 closes a light path between the photo emitter 52 and the photo detector 56, sending a signal to the controller 36 and activating the indicators 38 to denote that the brine solution is sufficiently concentrated. For example, the indicators 38 are optionally a green LED, an audible tone, or a combination of the above, although other indicators are contemplated.

However, when the density of the brine solution 16 is less than that of the float 62, the float is submerged in the first float cavity 60 (shown in solid lines in FIG. 2), keeping the light path between the photo emitter 52 and the photo detector 56 open and unobstructed, triggering the indicator 38 to alert the user, such as by a red LED and/or audible tone/alarm, that additional salt 20 is needed in the brine tank 12 or that a salt bridge may be present.

Specifically, the signal sent to the controller 36 is indicative of the position of the float 62 in the first float cavity 60. The photo detector 56 is configured for passing a voltage of between 0-4.5V to the controller 36, depending on the amount of light produced by the photo emitter 52 and the position of the float 62. The microprocessor (not shown) in the controller 36 is configured such that if the signal from the photo detector 56 is less than 2.5V, the float 62 is obstructing the light path and the brine solution 16 is adequately concentrated. Similarly, if the signal from the photo detector is greater than 2.5V, the light path is unobstructed and the indicators 38 alert the user that salt 20 needs to be added to the brine solution 16. For example, if the light path between the photo emitter 52 and the photo detector 56 is completely unobstructed, the photo detector will pass the maximum voltage of 4.5V to the controller 36, signifying that the float 62 is submerged and the salt needs to be replaced. However, it is recognized that other methods for alerting the user of the salt concentration may be suitable, depending on the application.

Still referring to FIG. 2, the second detector set 48 is configured for determining the flow rate of the brine solution 16 during the brine draw and refill cycles, and includes a first pair of detectors 66 including a first photo emitter 68 and a first photo detector 70, and a second pair of detectors 72 including a second photo emitter 74 and a second photo detector 76. The first and second photo emitters 68, 74 are preferably arranged in a photo emitter chamber 78, and the first and second photo detectors 70, 76 are arranged in a photo detector chamber 80 spaced apart from the photo detector chamber and defining a second float cavity 82 therebetween. As is the case with the first float cavity 60, the second float cavity 82 includes openings 83a, 83b that are in fluid communication with the brine solution 16 in the brine tank 12. It should be appreciated that the positions of the photo emitters and the photo detectors are reversible.

Preferably, and to ensure proper functioning of the second detector set 48, the first photo emitter 68 and the first photo detector 70 are arranged at the same height in their respective chambers 78, 80, respectively. Also, the second photo emitter 74 and the second photo detector 76 are arranged at the same height in their respective chambers 78, 80 and are vertically spaced apart from the first pair of detectors 66.

Preferably still, the first pair of detectors 66 is located at a level above the brine plate 26, and the second pair of detectors 72 is located at a level even with the brine plate. Both the first and second pairs of detectors 66, 72 are preferably provided above the brine valve 22 of the brine tank 12 (FIG. 1). It is contemplated that this configuration will provide accurate flow rate measurements.

A second float 84, preferably a ball-type float, is provided in the second float cavity 82, as seen in FIG. 2. The second float 84, similar to the float 62, has a specific density of less than 1.00, and is preferably manufactured of a corrosion-resistant polymer having the recited specific density, although other similar plastics or anti-corrosion materials may be appropriate.

During the brine draw cycle, the brine solution 16 is drawn from the brine tank 12 through an eductor nozzle (not shown), the conduit 24, an inflow conduit 86 and into the ion exchange resin 30 in the treatment tank 34. As the brine solution 16 is drawn from the brine tank 12, the solution level falls below the first pair of detectors 66 (i.e., the first pair of detectors 66 is exposed to the air within the tank 12). At this point, the second float 84 moves with the brine solution level, opening a light path between the first photo emitter 68 and the first photo detector 70, sending a signal to the controller 36, initiating a timer (not shown).

When the brine solution 16 level falls below the second pair of detectors 72 (i.e., the second pair of detectors is exposed to the air within the tank 12), the second float 84 is at a bottom 87 of the second float cavity 82 adjacent to the opening 83b, and closes a light path between the second photo emitter 74 and the second photo detector 76 (shown in dashed lines in FIG. 2), sending a signal to the controller 36 and stopping the timer. The time taken for the brine solution 16 to pass between the first and second pairs of detectors, 66, 72, respectively, can be used to determine the brine draw flow rate.

Specifically, the brine draw flow rate can be determined using the following equation:

$$FR_e = \{[\pi * h * r_1^2 * (\text{PerVoid})] + [(1-\text{PerVoid}) * (\pi * h) * (r_2^2)]\}/t_e$$

where:
$FR_e$=brine draw flow rate;
h=height between the photo emitter and photo detector;
$r_1$=radius of brine tank;
PerVoid=% volume of the tank occupied by salt (~45% for pellet salt);
$r_2$=radius of brine valve housing; and
$t_e$=time taken to reach distance h during the brine draw cycle Based on the brine draw flow rate, the user can determine whether the eductor nozzle, which enables the brine solution 16 to be drawn through the conduit 24, is plugged or partially blocked. Specifically, if the brine draw flow rate is below a predetermined level, there is a probability that the eductor nozzle is plugged or partially blocked and needs to be serviced, and the indicators 38 will alert the user, via an LED or audible alarm, for example.

During the refill cycle, soft water flows through an outflow conduit 88 and the conduit 24 and fills the brine tank 12 to prepare the brine solution 16 for the next regeneration. As the tank 12 refills, the solution level will first rise above the second pair of detectors 72, causing a decrease in frequency and resistance in the circuit connected to the second photo detector 76 and an increase in conductivity of the brine solution 16. Such an increase in conductivity of the brine solution 16 increases the concentration and density of the solution, causing the second float 84 to rise and open a light path between the second photo emitter 74 and the second photo detector 76, sending a signal to the controller 36 to start the timer.

When the solution level rises to the level of the first pair of detectors 66, the second float 84 is at a top 89 of the second float cavity 82 adjacent to the opening 83a and closes the light path between the first photo emitter 68 and the first photo detector 70, sending a signal to the controller 36 to stop the timer. Because of the increased conductivity of the brine solution 16, the density of the solution is greater than or equal to that of the second float 84, and the second float remains at the top 89 of the second float cavity 82. The time taken for the brine solution 16 to rise between the second and first pairs of detectors 72, 66, respectively, can be used to calculate the refill flow rate.

Specifically, the refill flow rate can be calculated using the following equation:

$$FR_r\{[\pi * h * r_1^2 * (\text{PerVoid})] + [(1-\text{PerVoid}) * (\pi * h) * (r_2^2)]\}/t_r$$

where:
$FR_r$=refill flow rate;
h=height between the photo emitter and photo detector;
$r_1$=radius of brine tank;
PerVoid=% volume of the tank occupied by salt (~45% for pellet salt);
$r_2$=radius of brine valve housing; and
$t_r$=time taken to reach distance h during the refill cycle Accordingly, based on the refill flow rate, the user can determine whether the refill flow controls/lines (not shown) in the conduit 24 are plugged or partially blocked. In particular, if the refill flow rate is below a predetermined level, there is a probability that the refill flow controls/lines are plugged or partially blocked, and the indicators 38 will alert the user via an LED or an audible alarm, for example, that the system must be serviced.

The first and second pairs of detectors 66, 72 can also be used to detect the presence of a salt bridge. As known in the art, salt bridges lead to low concentration brine under the salt bridge and ineffective ion exchange reaction during regeneration, resulting in a reduction of service capacity and hardness leakage. To detect the presence of a salt bridge, the timer is started at the beginning of the fast rinse cycle, and when the level of the brine solution 16 rises to the second pair of detectors 72, the second float 84 is at the bottom 87 of the second float cavity 82 and closes the light path between the second pair of detectors, sending a signal to the controller 36 and stopping the timer. Based on this time, the average velocity below the second pair of detectors 72 can be determined utilizing the following equation:

$$v_1 = FR_r / \{(\pi * r_1^2) - [(1 - \text{PerVoid}) * (4 * \pi * [(R_a + R_b)/2]^2)]\}$$

where:
$v_1$ = average velocity below the second pair of detectors;
$FR_r$ = refill flow rate;
$r_1$ = radius of brine tank;
$R_a$ = larger radius of brine plate leg 28b (FIG. 1);
$R_b$ = smaller radius of brine plate leg 28b (FIG. 1); and
PerVoid = % volume of tank occupied by salt (~45% for pellet salt)

When the brine solution level rises past the second pair of detectors 72, the concentration and density of the solution 16 is increasing, and the second float 84 moves upward in the second float cavity 82, opening the light path between the second photo emitter 74 and the second photo detector 76 and sending a signal to the controller 36, initiating the timer. When the solution level reaches the first pair of detectors 66, the second float 84 is at the top 89 of the second float cavity 82 and closes the light path between the first photo emitter 68 and the first photo detector 70, stopping the timer. Based on this time, the average velocity above the second pair of detectors 72 is calculated using the following equation:

$$v_2 = FR_r / \{[((\pi * r_1^2) - (\pi * r_2^2)) * (\text{PerVoid})] + (\pi * r_2^2)\}$$

where:
$v_2$ = average velocity above the second pair of detectors;
$FR_r$ = refill flow rate;
$r_1$ = radius of brine tank;
$r_2$ radius of brine valve housing;
$R_a$ = larger radius of brine plate leg of right cone (FIG. 1);
$R_b$ = smaller radius of brine plate leg of right cone (FIG. 1); and
PerVoid = % volume of tank occupied by salt (~45% for pellet salt)

A velocity ratio between the velocity above the second pair of detectors 72 and the velocity below the second pair of detectors can then be calculated as follows:

$$v_{ratio} = (d_2/t_r)/(d_1/t_o) \approx 1.6$$

where:
$v_{ratio}$ = velocity ratio based on a 250 pound tank;
$d_2$ = distance between first and second pairs of detectors;
$t_r$ = time taken to reach first detector from second detector;
$d_1$ = distance between beginning brine level and second detector; and
$t_o$ = time taken to reach second detector from beginning of fast rinse cycle In a properly operating system, because of the volume occupied by the salt 20 (FIG. 1), the velocity above the second pair of detectors 72 is generally greater than that below the second pair of detectors. However, if the velocity ratio is below 1.6 (the approximate desired velocity ratio based on a 250 pound tank), the indicators 38 alert the user that the probability of a salt bridge is high because a low velocity ratio indicates inadequate salt concentration in the brine solution 16.

As stated above, the present salometer and flow rate sensor assembly provides a first detector set 46 for determining whether the brine solution 16 is sufficiently concentrated to indicate the need for salt replenishment, and/or a second detector set 48 for determining the brine draw and refill flow rates of the solution during regeneration to determine when the water softener system 14 needs servicing. The first and second detector sets 46, 48 are preferably provided in a single sensor housing 40, rather than in two separate housings, and accordingly the wiring 44 emanates from the same source and only one sensor assembly 10 needs to be provided in the brine tank 12. However, multiple housings are contemplated depending on the application.

While a particular embodiment of the present salometer and flow rate sensor assembly has been described herein, it will be appreciated by those skilled in the art that changes and modifications may be made thereto without departing from the invention in its broader aspects and as set forth in the following claims.

What is claimed is:

1. A flow sensor for a water softener system including a brine tank containing a brine solution, the flow sensor being mounted in the brine tank and comprising:
   a housing;
   a first pair of detectors in said housing;
   a second pair of detectors in said housing, said second pair of detectors being spaced from said first pair of detectors;
   a movable float located in a cavity defined by said housing;
   a timer in communication with said first pair and said second pair of detectors, wherein said timer is started when said float moves a designated distance below said first pair of detectors, and wherein said timer stops when said float is detected by said second pair of detectors;
   a controller in communication with said first pair of detectors, said second pair of detectors and said timer, and configured to start said timer when said float moves the designated distance below said first pair of detectors and stop said timer when said float is detected by said second pair of detectors, said controller configured to determine a first brine solution velocity above said second pair of detectors and a second brine solution velocity below said second pair of detectors based on a difference in time between when said timer started and when said time stopped, and a velocity ratio between said first and said second brine solution velocities; and
   at least one indicator on said controller, said indicator configured to indicate a probability of a salt bridge based on said velocity ratio determined by said controller.

2. The flow sensor of claim 1, wherein said first pair of detectors and said second pair of detectors each include at least one photo emitter and at least one photo detector, each of said photo emitters configured to generate and direct light toward a corresponding photo detector.

3. The flow sensor of claim 2, wherein each of said photo emitters generates an infrared light and each of said photo detectors passes an electrical current that is directly proportional to an intensity level of said infrared light.

4. The flow sensor of claim 1, wherein said float is a ball-type float.

5. A method for determining a flow rate of a brine solution in a brine tank, the brine tank including a sensor housing having a first pair of detectors including a first photo emitter and a first photo detector, a second pair of detectors including a second photo emitter and a second photo detector, a movable float located in a cavity between the first and second photo emitters and the first and second photo detectors and a timer in communication with the first and second pairs of detectors, said method comprising the steps of:
   starting the timer when the float is at a first position relative to the first and second pairs of detectors;
   stopping the timer when the float is at a second position relative to the first and second pairs of detectors;
   determining a total time taken for the float to move from said first position to said second position;

determining a first brine solution velocity above said second pair of detectors and a second brine solution velocity below said second pair of detectors based on the total time;

determining a velocity ratio between said first and said second brine solution velocities; and indicating a probability of a salt bridge in the brine tank based on the velocity ratio.

6. The method of claim 5, wherein the step of calculating said flow rate includes calculating a brine draw flow rate using the following equation:

$$FR_e = \{[\pi * h * r_1^2 *(\text{PerVoid})] + [(1-\text{PerVoid})*(\pi * h)*(r_2^2)]\}/t_e$$

where:
$FR_e$=brine draw flow rate;
h=height between the photo emitter and photo detector;
$r_1$=radius of brine tank;
Per Void=% volume of the tank occupied by salt (~45% for pellet salt);
$r_2$=radius of brine valve housing; and
$t_e$=time taken to reach distance h during the brine draw cycle.

7. The method of claim 5, wherein the step of calculating said flow rate includes calculating a brine refill flow rate using the following equation:

$$FR_r = \{[\pi * h * r_1^2 *(\text{PerVoid})] + [(1-\text{PerVoid})*(\pi * h)*(r_2^2)]\}/t_r$$

where:
$FR_r$=refill flow rate;
h=height between the photo emitter and photo detector;
$r_1$=radius of brine tank;
PerVoid=% volume of the tank occupied by salt (~45% for pellet salt);
$r_2$=radius of brine valve housing; and
$t_r$=time taken to reach distance h during the refill cycle.

8. The method of claim 5, which includes activating at least one indicator when the brine flow draw rate is at a designated flow rate.

9. A method for determining the presence of a salt bridge in a brine solution stored in a brine tank, the brine tank including a sensor housing having a first pair of detectors including a first photo emitter and a first photo detector, a second pair of detectors including a second photo emitter and a second photo detector, and a movable float located in a cavity between the first and second photo emitters and the first and second photo detectors and a timer in communication with the first and second pairs of detectors, said method comprising the steps of:

starting the timer when the float is at a first position relative to the first pair of detectors;

stopping the timer when the float is at a second position relative to the second pair of detectors;

determining a total time taken for the float to move from said first position to said second position;

calculating a first average velocity of the brine solution below the second pair of detectors;

calculating a second average velocity of the brine solution above the second pair of detectors;

determining a velocity ratio based on said first average velocity and said second average velocity; and activating at least one indicator when said velocity ratio is at a designated velocity ratio.

10. The method of claim 9, wherein said first average velocity is calculated using the following equation:

$$v1 = FRr/\{(\pi * r12) - [(1-\text{PerVoid})*(4*\pi*[(Ra+Rb)/2]2)\}$$

where:
v1=average velocity below the second pair of detectors;
FRr=refill flow rate;
r1=radius of brine tank;
Ra=larger radius of brine plate leg 28b (FIG. 1);
Rb=smaller radius of brine plate leg 28b (FIG. 1); and
PerVoid=% volume of tank occupied by salt (~45% for pellet salt).

11. The method of claim 9, wherein said second average velocity is calculated using the following equation:

$$v_2 = FR_r/\{[((\pi * r_1^2)-(\pi * r_2^2))*(\text{PerVoid})]+(\pi * r_2^2)\}$$

where:
$v_2$=average velocity above the second pair of detectors;
$FR_r$=refill flow rate;
$r_1$=radius of brine tank;
$r_2$ radius of brine valve housing;
$R_a$=larger radius of brine plate leg of right cone (FIG. 1);
$R_b$=smaller radius of brine plate leg of right cone (FIG. 1);and
PerVoid=% volume of tank occupied by salt (~45% for pellet salt).

* * * * *